(12) United States Patent
Ko

(10) Patent No.: US 7,754,693 B2
(45) Date of Patent: Jul. 13, 2010

(54) COMPOSITION AND METHOD FOR THE EFFICACIOUS AND SAFE ADMINISTRATION OF HALOPYRUVATE FOR THE TREATMENT OF CANCER

(76) Inventor: Young Hee Ko, 5006 Gold Hill Rd., Owings Mills, MD (US)

( * ) Notice: Subject to any disclaimer, the term of this patent is extended or adjusted under 35 U.S.C. 154(b) by 820 days.

(21) Appl. No.: 11/706,868

(22) Filed: Feb. 14, 2007

(65) Prior Publication Data

US 2007/0203074 A1    Aug. 30, 2007

Related U.S. Application Data

(60) Provisional application No. 60/773,653, filed on Feb. 16, 2006.

(51) Int. Cl.
*A61K 31/70* (2006.01)
*A61K 31/715* (2006.01)
*A61K 31/19* (2006.01)

(52) U.S. Cl. .............................. 514/23; 514/53; 514/54; 514/557

(58) Field of Classification Search ................ 514/23, 514/53, 54, 557
See application file for complete search history.

(56) References Cited

U.S. PATENT DOCUMENTS

| 5,759,837 | A | 6/1998 | Kuhajda et al. |
| 6,031,000 | A | 2/2000 | Nissen et al. |
| 2003/0087961 | A1 | 5/2003 | Ko et al. |
| 2004/0126789 | A1 | 7/2004 | Park et al. |

OTHER PUBLICATIONS

Ko, Y.H. et al., Advanced cancers: eradication in all cases using 3-bromopyruvate therapy to deplete ATP, Biochemical and Biophysical Research Communications, 2004, 324, 269-275.

*Primary Examiner*—Raymond J Henley, III
(74) *Attorney, Agent, or Firm*—Thorpe North & Western LLP

(57) ABSTRACT

This invention provides compositions and methods for the treatment of cancer. An inhibitor cocktail buffer includes at least one sugar, a non-potassium containing buffer, and an inhibitor having the general formula:

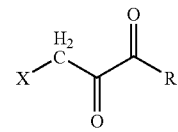

Such an inhibitor cocktail buffer allows for the efficacious and safe delivery of various compounds, including halopyruvates and derivatives thereof, to human cancer patients.

54 Claims, No Drawings

COMPOSITION AND METHOD FOR THE EFFICACIOUS AND SAFE ADMINISTRATION OF HALOPYRUVATE FOR THE TREATMENT OF CANCER

RELATED APPLICATIONS

This application claims the benefit and priority of Provisional Application Ser. No. 60/773,653, filed Feb. 16, 2006, and entitled "A Composition And Method For The Efficacious And Safe Administration Of Halopyruvate For The Treatment Of Cancer."

FIELD OF THE DISCLOSURE

Compositions and methods are disclosed for treatment of numerous cancers with a halopyruvate. As such, the present invention involves the fields of chemistry, pharmacology, and biology.

BACKGROUND OF THE DISCLOSURE

Perhaps no other word or diagnosis strikes as much fear into a patient as cancer. Each year, hundreds of thousands of men, women, and children in the United States die of some form of cancer. Worldwide, millions die of cancers including those of the bone, bladder, blood (leukemias), brain, breast, colon, cervix, esophagus, intestine, kidney, liver, lung, mouth, nose, nerves, ovaries, pancreas, prostate, skin, stomach, testis, throat, thyroid, uterus, and vagina.

Over the years, a number of methods have been used to treat cancer including radiation and chemotherapy. The primary goal of these treatments is to kill all the cancer cells. However, many healthy cells are invariably destroyed in a race to kill the cancer cells before the treatment(s) kill the patient. Even today, the more measured and quantitative uses of radiation and chemotherapy can cause illness and even death in some patients. At the same time, in some types of cancer, the malignant cells remain difficult to treat. Consequently, the physiology or phenotypes of cancer cells have been extensively studied to identify new targets that can be selectively attacked to kill the cancer cells without adversely affecting the healthy cells of the patient.

It was suggested in U.S. Pat. No. 5,759,837 that fatty acid synthase ("FAS") is overexpressed in carcinomas with a poor prognosis, but much less FAS expression is identified in normal tissues. U.S. Pat. No. 5,759,837 stated also that inhibition of fatty acid synthesis is selectively toxic to carcinoma cells, while normal cells with low FAS activity are resistant. A possible method of treating cancer patients where fatty acid synthesis by cells of the patient's tumor is inhibited with resultant interruption of the disease process is taught. Although one of the suggested inhibitors was 3-bromopyruvate ("3-BrPA"), no experiments using 3-BrPA for cancer therapy in animals was provided, and there was no mention of how it can be formulated for use in humans.

Significantly, one of the most common, profound, and intriguing phenotypes of highly malignant tumors, known for more than seven decades, is their ability to metabolize glucose at high rates in order to synthesize high levels of ATP to energize tumor growth. Under aerobic conditions more than half the ATP produced in such tumor cells may be derived via glycolysis, in sharp contrast to normal cells, where this value is usually less than 10% with oxidative phosphorylation serving as the predominant method for ATP generation. Under hypoxic (low oxygen tension) conditions, frequently present within the tumor, the already high glycolytic rate may double, allowing the tumor cells to thrive as neighboring normal cells become growth deficient. This is a characteristic of most animal and human tumors and usually occurs at an advanced poorly differentiated stage in their progression. In fact, it is known that a close correlation exists among the degrees of differentiation, growth rate, and glucose metabolism of tumors, where those that are the most poorly differentiated exhibit the fastest growth and the highest glycolytic rate. Noteworthy is the fact that this unique "high glycolytic" phenotype is used clinically worldwide in Positron Emission Tomography ("PET") to detect tumors, assess their degree of malignancy, predict survival times, and assess the relative effectiveness of various treatments.

Despite the commonality of the high glycolytic phenotype and its widespread use clinically as a diagnostic tool, only recently has it been exploited as a major target for arresting or slowing the growth of cancer cells. This is because the underlying molecular basis of the high glycolytic phenotype, long suspected to involve some type of mitochondrial-glycolytic interaction, has only recently become understood. Thus, experiments have demonstrated a requirement for an overexpressed mitochondrially bound form of hexokinase, now identified as Type II hexokinase.

U.S. Patent Application Publication No. 20030087961 (Ko et al.) teaches that 3-BrPA is a potent energy blocker, inhibiting both ATP production sources (glycolysis and mitochondria) of tumor cells in vitro, and when delivered intra-arterially directly to a tumor site within the liver of an experimental animal (rabbit) has an impressive killing capacity in a single injection with no more than 10-16% of the tumor cells remaining alive.

A subsequent publication continued to suggest the use of a halopyruvate as a highly effective primary component in a pharmaceutical composition or treatment regimen for cancer. Specifically, Ko (Ko, Y. H. et al., *Biochemical Biophysical Research Communications* 324, 269-275, 2004, incorporated herein by reference) achieved complete eradication of advanced "PET Positive" hepatocellular carcinomas ("HCCs") in a rat model using 3-BrPA therapy. Repeated injections were made of a 2 mM solution in 1×PBS (potassium phosphate buffered saline pH 7.5) directly at the tumor site. Normal tissue was unaffected as it has little propensity to take up the 3-BrPA in contrast to PET POSITIVE cancers that take up 3-BrPA and then cause cell ATP depletion followed by cell death. (PET POSITIVE tumors exhibit a positive PET scan indicating that they exhibit a rapid metabolism of glucose converting this sugar to lactic acid that is transported out of the cancer cells on specific transporters referred to here as the "lactic acid transporter." As 3-BrPA is very structurally similar to lactate, the applicant et al. proposed that 3-BrPA likely enters cancer cells via the "lactic acid transporter", and once inside because of its strong alkylating nature inhibits both glycolysis and mitochondrial function thus resulting in almost total cell ATP depletion and rapid cell death.)

In Ko (2004), the tumor cells had been implanted externally or in the abdominal cavity. Thus, it was possible for 3-BrPA in a freshly prepared solution (i.e., in phosphate buffered saline) to be applied directly at or near the tumor site. However, most PET POSITIVE human cancers occur in organs located internally in the body, thus emphasizing the need for a therapeutic cocktail formulated for human delivery.

SUMMARY OF THE DISCLOSURE

Despite the remarkable success achieved in the above animal studies using 3-bromopyruvate as an anticancer agent, it has been recognized by the inventor that it is very important to make modifications in the therapeutic cocktail prior to treatment of humans to assure that: 1) the 3-BrPA is stable in a clinical setting; 2) that the 3-BrPA is not painful (irritating) upon injection; and 3) that the therapeutic cocktail to be injected poses little or no problem related to toxicity to the patient. In order to overcome the three above noted potential problems with 3-BrPA, it is first important to understand the nature of the problems. First, 3-BrPA is potentially unstable because of solvolysis in aqueous solutions that tends to dissociate (remove) the halide ion rendering the agent ineffective. Secondly, because 3-BrPA is an acid, it has the potential of causing irritation or pain upon injection. Finally, the injection cocktail containing 3-BrPA as used in the above referenced animal studies, although remarkably successful in the animal studies, would be inappropriate for human delivery as a potassium phosphate buffered saline solution was used, and potassium has been shown to exhibit toxicity (hyperkalemia) in some human studies (Wetli, C. V. and Davis, J. H., *J. American Medical Association*, 240, 1339, 1978; Restuccio, A., *American Journal of Emergency Medicine*, 10, 171-173, 1992).

The present invention provides a stable, non-irritant, safe, and highly effective halopyruvate therapeutic "stock" cocktail for the treatment of cancers, and especially cancers in humans, that have been diagnosed as Positron Emission Tomography positive, i.e., "PET" positive. This would include the vast majority of human cancers, particularly those that have reached an advanced stage. Solvolysis, and therefore inactivation of the halopyruvate as well as its pain/irritability-like acidity, has been minimized in the therapeutic cocktail described here by both replacing much of the water with the sugar/sugar-like molecules sorbitol, inositol, and glycerol, and including a higher concentration of buffer than used previously. This assures that the halopyruvate will remain stable for a longer period of time both prior to and after its dilution and injection into a patient in the clinic/hospital setting and therefore assures also that a greater number of intact halopyruvate molecules reach their tumor target(s). It also reduces the possibility of pain/irritability upon injection. In addition, by using a non-potassium containing buffer, e.g., a sodium phosphate buffer, potential heart and other problems related to potassium toxicity are eliminated.

Very significantly, the novel therapeutic cocktail disclosed in this application has been carefully designed and formulated to overcome the three potential problems noted above. Specifically, water has been significantly replaced with the sugar/sugar-like molecules sorbitol, inositol, and glycerol in order to suppress water-induced solvolysis and enhance stability of the 3-BrPA (Table 1). In addition, the buffer concentration has been increased to reduce acidity and therefore pain/irritability upon injection. Finally, by replacing the original potassium phosphate buffer with a sodium phosphate buffer the possibility of toxicity due to injected potassium is eliminated. 3-BrPA contained in this novel therapeutic cocktail has been shown to be highly effective in killing most cancer cells, including cells within 7 different human cancer cell lines tested in tissue culture to date. In fact, 3-BrPA in this novel therapeutic cocktail has been shown to be far superior in this capacity to a number of other anti-cancer agents (carboplatin, cyclophosphamide, doxorubicin, 5-fluorouracil, methotrexate, and taxol) that are routinely used clinically to treat human cancer patients (Table 2).

In one embodiment of the disclosure, the halopyruvate therapeutic stock cocktail solution further comprises a high percentage of sorbitol and/or other sugar. The percentage sugar in the solution can be higher than 50%.

In another embodiment of the disclosure, the halopyruvate stock cocktail solution further comprises glycerol and a second sugar.

In another embodiment of the disclosure, the 3-halopyruvate therapeutic "stock" cocktail concentration will be greater than 0.5 M. Then, when the halopyruvate is added to a diluted solution or pharmaceutical carrier, any disassociation of the halide will be slowed. This allows for a more efficacious pharmaceutical because more of the halopyruvate will reach the target cancer cells.

In another embodiment of the disclosure, other inhibitors of cancer cell ATP production are represented by the formula:

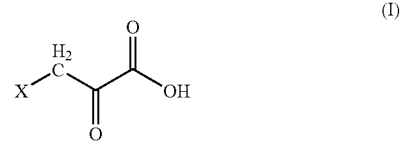

(I)

wherein X represents a halide, a sulfonate, a carboxylate, an alkoxide, or an amine oxide.

In another aspect, the disclosure provides selective inhibitors of ATP production represented in the general formula:

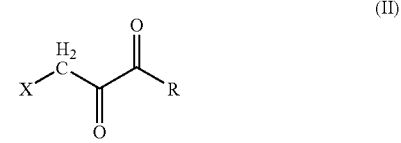

(II)

wherein X represents a halide, sulfonate, a carboxylate, an alkoxide, or amine oxide and R represents OR', H, N(R")$_2$, C1-C6 alkyl, C6-C12 aryl, C1-C6 heteroalkyl, or a C6-C12 heteroaryl. Independently, in other embodiments, R" represents H, C1-C6 alkyl, or C6-C12 aryl. Independently, in still other embodiments, R or R' represents H, alkali metal, C1-C6 alkyl, C6-C12 aryl or C(O)R'''; and R''' represents H, C1-C20 alkyl or C6-C12 aryl.

The present invention further provides pharmaceutical compositions comprising the subject inhibitors. In certain embodiments, the pharmaceutical composition preferably comprises one or more of the inhibitors.

In still other embodiments, the pharmaceutical composition comprises one or more of the inhibitors, and a second chemotherapeutic agent. In yet another embodiment, the pharmaceutical composition comprises one or more of the inhibitors, and a scavenger compound.

The present invention further provides novel therapeutic methods of treating a cancerous tumor comprising administering to the subject an effective amount of a subject pharmaceutical composition comprising an effective amount of a selective inhibitor of ATP synthesis. In certain embodiments, the method comprises parenterally administering a subject composition to a subject. In one embodiment, the method comprises intraarterial administration of a subject composition to a subject. In one embodiment, the method comprises administering an effective amount of a subject composition directly to the arterial blood supply of the cancerous tumor. The intraarterial delivery of the ATP synthesis inhibitor directly to the blood supply of the tumor may be done in conjunction with embolization of the tumor [i.e., occluding (closing), or at least drastically reducing, blood flow to one or more blood vessels supplying the tumor]—i.e., "chemoembolization." In a preferred embodiment, the ATP synthesis inhibitor can be administered directly to the blood supply of the tumor without embolization of the tumor. Where dilution of the inhibitor cocktail buffer is necessary, the buffer can prevent or limit disassociation of the halide.

In another preferred embodiment of the disclosure, the cancerous tumor can be a liver tumor. In still other embodiments, the method comprises systemic administration of a subject composition to a subject. In certain embodiments, the methods of treating a cancerous tumor comprise administering a subject inhibitor and administering a second agent to a subject. Such administration may be simultaneous or sequential. In one embodiment, the second agent can be a chemotherapeutic agent. In another embodiment, the second agent can be a scavenger compound. In certain embodiments, the second agent may be formulated into a separate pharmaceutical composition. In other embodiments, the inhibitor and second agent are co-formulated into a pharmaceutical composition.

In other embodiments, this disclosure contemplates a kit including subject pharmaceutical compositions, including the buffers, and optionally instructions for their use. Uses for such kits include, for example, therapeutic applications. In certain embodiments, the subject compositions contained in any kit have been lyophilized and require rehydration before use. In other embodiments, the various components, except for the necessary basic buffer or sterilized water, are kept in a dry sterile form.

Before proceeding further, a definition of the terms used and their applicability to the disclosure is needed:

The articles "a" and "an" are used herein to refer to one or to more than one (i.e., to at least one) of the grammatical object of the article. By way of example, "an element" means one element or more than one element.

The terms "library" or "combinatorial library" refer to a plurality of molecules, which may be termed "members," synthesized or otherwise prepared from one or more starting materials by employing either the same or different reactants or reaction conditions at each reaction in the library. In general, the members of any library show at least some structural diversity, which often results in chemical and biological diversity. Such structural diversity in preparing libraries of coordination molecules may include, by way of example, metal ion diversity, ligand diversity, solvation diversity or counter-ion diversity. A library may contain any number of members from two different members to about $10^8$ members or more. In certain embodiments, libraries of the present disclosure have more than about 12, 50, and 90 members. In certain embodiments of the present disclosure, the starting materials and certain of the reactants are the same, and chemical diversity in such libraries is achieved by varying at least one of the reactants or reaction conditions during the preparation of the library. Combinatorial libraries of the present disclosure may be prepared in solution or on the solid phase. Further details regarding the libraries of the present disclosure are described below.

"Modulation" refers to up regulation (i.e., activation or stimulation), down regulation (i.e., inhibition or suppression) of a response, or the two in combination or apart.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

A "patient" or "subject" or "host" refers to either a human or nonhuman animal. The "nonhuman animals" of the disclosure comprise any nonhuman animal that is capable of expressing the subject genes and gene products. Such nonhuman animals include vertebrates such as rodents, nonhuman primates, ovines, bovines, ruminants, lagomorphs, porcines, caprines, equines, canines, felines, aves, piscines, etc. In certain embodiments of the disclosure, the animals are mammals. Exemplary nonhuman mammals are porcines (e.g., pigs), murines (e.g., rats, mice, and lagomorphs (e.g., rabbits)), and nonhuman primates (e.g., monkeys and apes).

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body.

"Pharmaceutically-acceptable salts" refers to the relatively nontoxic, inorganic and organic acid addition salts of compounds.

The phrase "selective inhibitor of ATP production" refers to any compound that is able to specifically modulate the activity of hexokinase or another enzyme (e.g., glycolytic or mitochondrial) that is required in the rapid ATP production that provides for the rapid growth of a cancerous tumor. For example, such metabolic pathways include the glycolytic pathway, and oxidative phosphorylation.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

"Therapeutic agent" or "therapeutic" refers to an agent capable of having a desired biological effect on a host. Chemotherapeutic and genotoxic agents are examples of therapeutic agents that are generally known to be chemical in origin, as opposed to biological, or cause a therapeutic effect by a particular mechanism of action, respectively. Examples of therapeutic agents of biological origin include growth factors, hormones, and cytokines. A variety of therapeutic agents is known in the art and may be identified by their effects. Certain therapeutic agents are capable of regulating red cell proliferation and differentiation. Examples include chemotherapeutic nucleotides, drugs, hormones, nonspecific (nonantibody) proteins, oligonucleotides (e.g., antisense oligonucleotides that bind to a target nucleic acid sequence (e.g., mRNA sequence)), peptides, and peptidomimetics.

"Therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present disclosure may be administered in a sufficient amount to produce a desired local or systemic effect at a reasonable benefit/risk ratio applicable to such treatment.

The phrase "therapeutically-effective amount" as used herein means that amount of a compound, material, or composition comprising a compound of the present disclosure which is effective for producing some desired therapeutic effect in at least a sub-population of cells in an animal at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented.

The phrase "about" as used herein is meant to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

Other features and advantages of the disclosure will be apparent from the following detailed description, and from the claims.

DETAILED DESCRIPTION OF THE DISCLOSURE

Inhibitors of ATP production are represented in the general formula:

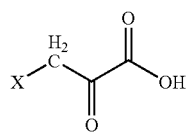

wherein X represents a halide, a sulfonate, a carboxylate, an alkoxide, or an amine oxide. In certain embodiments, X can be a halide selected from the group consisting of: fluoride, bromide, chloride, and iodide. In one embodiment, the inhibitor can be a 3-halopyruvate. In certain embodiments, the 3-halopyruvate can be selected from the group consisting of: 3-fluoropyruvate, 3-chloropyruvate, 3-bromopyruvate, and 3-iodopyruvate. In one embodiment, the 3-halopyruvate can be 3-bromopyruvate. In other embodiments, X can be a sulfonate selected from the group consisting of: triflate, mesylate and tosylate. In yet another embodiment, X can be an amine oxide. In one embodiment, X can be dimethylamine oxide.

In another aspect, the disclosure provides selective inhibitors of ATP production represented in the general formula:

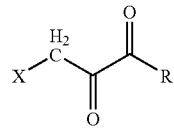

wherein X represents a halide, a sulfonate, a carboxylate, an alkoxide, or an amine oxide. In certain embodiments, X can be a halide selected from the group consisting of: fluoride, bromide, chloride, and iodide. In other embodiments, X can be a sulfonate selected from the group consisting of: triflate, mesylate and tosylate. In yet another embodiment, X can be an amine oxide. In one embodiment, X can be dimethylamine oxide. In certain embodiments R represents OR', H, N(R")$_2$, C1-C6 alkyl, C6-C12 aryl, C1-C6 heteroalkyl, or a C6-C12 heteroaryl. Independently, in other embodiments, R" represents H, C1-C6 alkyl, or C6-C12 aryl. Independently, in still other embodiments, R or R' represents H, alkali metal, C1-C6 alkyl, C6-C12 aryl or C(O)R'''; and R''' represents H, C1-C20 alkyl or C6-C12 aryl.

Many or most of the inhibitors above function as analogs to pyruvic acid or pyruvate. Similar to 3-BrPA, they inhibit ATP production in the cells. More specifically, they serve as selective inhibitors of ATP production, affecting the glycolytic pathway and oxidative phosphorylation. Once the glycolytic pathway and oxidative phosphorylation are shut down, ATP production stops and the cells lyse and die. When a patient is treated with one or more of the above inhibitors, cancer cells having increased growth rate and metabolism will show an increase in cell death.

While some of the inhibitors, such as 3-fluoropyruvate or 3 sulfonate pyruvate can, theoretically, have a lower rate of disassociation (i.e., of the fluoride or sulfonate), other compounds, such as 3-bromopyruvate, 3-chloropyruvate, or 3-amine oxide pyruvate, can have a very high rate of disassociation (i.e., of the bromide, chloride, or 3-amine-oxide). Under most conditions, once the structure on the tertiary carbon has disassociated, the remaining chemical structure reverts to pyruvate.

The inhibitor of choice may preferably be added to the cocktail buffer to form what may be called the inhibitor cocktail buffer or "therapeutic cocktail." The components forming the cocktail buffer prevent or extremely limit the disassociation of the inhibitor compound, i.e., the removal of the bromide or other halide, or the removal of, for example, a sulfonate or 3-amine-oxide group as indicated above.

The cocktail can be prepared as follows:

First, a 0.5 M sodium phosphate solution having a range of from about 0.1 to about 0.75 M, and preferably about 0.5 M can be prepared at room temperature. The pH of the solution cab be in the range of about 6.8 to about 7.8, but preferably about pH 7.4. In an alternative embodiment of the disclosure, sodium carbonate may be used instead of sodium phosphate; however, sodium phosphate is more physiologically acceptable.

Additionally, glycerol can be included as part of the solution. The amount of glycerol in the solution may range from about 0% to about 3%, with about 1% being the optimum amount of glycerol. In one embodiment, the amount of glycerol in the solution may range from about 0.1% to about 3%. The replacement of water by glycerol serves to limit the solvolysis of 3-bromopyruvate and similar said structured inhibitors. The final concentrations of glycerol to be used is below the toxicity levels.

The solution can also contain from about 1 to about 5% inositol and from about 30 to about 55% sorbitol. The total of the upper range of the percentages of the sugars generally represents the maximum solubility of each sugar alcohol. The large amount of sugar greatly reduces solvolysis of the inhibitor. Additionally, it can be preferable that a five carbon sugar be used in large volumes, as opposed to a six carbon sugar, so as to not elicit an insulin response which might promote cancer growth.

The large volume of sugar takes up volume that would normally be water in the phosphate solution, which in turn would have caused solvolysis. By having a high volume of sugar, the amount of water can be reduced, thereby reducing the amount of solvolysis.

In one preferred embodiment of the disclosure, the halopyruvate therapeutic "stock" cocktail can comprise 0.5 M sodium phosphate (pH 7.4), 1% glycerol, 4% inositol, and 55% sorbitol at room temperature (25° C.) after which the solution can be chilled on ice to increase stability and decrease the rate of solvolysis.

Once the cocktail has been chilled, the inhibitor (such as 3-bromopyruvate) can be added in sufficient amounts to give a final concentration of about 0.1 to about 0.75 M of inhibitor, and preferably about 0.5 M. The solution can be shaken vigorously until all 3-bromopyruvate is dissolved.

The stock solution can then be sterilized, preferably with a 0.22 micron filter unit, and then preferably chilled to prevent solvolysis.

This stock solution can then be quickly diluted about 500 to 1,000 times with a saline solution at room temperature. The solution is then ready for injection (i.p., i.v., s.c. or i.t.) into the subject where i.p. is intraperitoeal; i.v. is intravenous; s.c. is subcutaneous; and i.t. is intratumoral.

The inhibitor can resist solvolysis up to one to three hours. Within that time period, and preferably within the first 20 minutes, the solution can be injected (i.p., i.v., s.c., or i.t.) into the subject. In one embodiment, 50% of the inhibitor can resist solvolysis for two hours. In another embodiment, 95% of the inhibitor can resist solvolysis for two hours.

In the example shown in Table 1, a cocktail buffer comprised of 0.5 M sodium phosphate (pH 7.4), 1% glycerol, 4% inositol, and 55% sorbitol maintained about 100% of the 3-bromopyruvate intact for two hours at 37 degrees C. Table 1 shows the relative stability index of each of the individual components of the cocktail buffer and the relative stability index of the example cocktail buffer. It also shows the relative stability index of water for comparison.

TABLE 1

RELATIVE INDEX OF STABILITY OF 3-BROMOPYRUVATE USING DIFFERENT AGENTS IN THE MEDIUM

| Condition # | Agent(s), Concentration | Relative Stability Index* |
|---|---|---|
| 1 | Water only | 0.33 |
| 2 | Glycerol, 1% | 0.34 |
| 3 | Inositol, 4% | 0.44 |
| 4 | Sorbitol, 55% | 0.47 |
| 5 | Sodium Phosphate, pH 7.4, 0.5 M | 0.17 |
| 6 | All four agents above | 1.00 |

As used here, the relative stability index refers to that fraction of 3-bromopyruvate that remains in the medium after 2 hours at 37 degrees C. It will be noted that the presence of all four agents in the example maintains 3-bromopyruvate as an intact, highly reactive molecule. This allows many such molecules to enter cancer cells (PET Positive) and quickly kill them. Because 3-bromopyruvate does not enter normal cells, or enters them very poorly/slowly, most are spared while the cancer cells are killed. The agents used for stabilizing 3-bromopyruvate, are commonly available, relatively inexpensive, and nontoxic in humans at the very low levels used.

In alternative embodiments of the invention, other sugar alcohols that can be substituted included but are not limited to erythritol, isomalt, lactitol, maltitol, sorbitol, xylitol, dulcitol, ribitol, inositol, and combinations thereof.

The inhibitors of the invention have been found to be very potent anticancer agents. For example, the capacity of 3-bromopyruvate to inhibit human lung cell proliferation in 24 hours relative to that of other well known anticancer agents commonly used as cancer therapy in humans is shown in Table 2. The 3-bromopyruvate was dissolved in the cocktail buffer referred to in Table 1, condition # 6, i.e., a cocktail buffer comprised of 0.5 M sodium phosphate (pH 7.4), 1% glycerol, 4% inositol, and 55% sorbitol.

TABLE 2

Capacity of Anticancer Agent 3-Bromopyruvate to Inhibit Human Lung Cell Proliferation in 24 Hours Relative to That of Other Well Known Anticancer Agents Commonly Used as Cancer Therapy in Humans

| Condition # | Anticancer Agent at 50 μM, for 24 hrs | Inhibition of Cell Proliferation, % |
|---|---|---|
| 1 | None (Control) | 0 |
| 2 | 3-Bromopyruvate | 92.5 |
| 3 | Carboplatin | 4.5 |
| 4 | Cyclophosphamide | 0 |
| 5 | Doxorubicin | 39.6 |
| 6 | 5-Fluorouracil | 17.8 |
| 7 | Methotrexate | 28 |
| 8 | Paclitaxel | 0* |

It will be noted from Table 2 that under the conditions used, 3-Bromopyruvate is by far more effective than the six other anticancer agents commonly used to treat human cancer. (Similar studies with a number of other human cancer cell lines have been conducted also). It is interesting to note that Paclitaxel promoted human lung cancer cell proliferation under the conditions used in this experiment, a disturbing finding considering the wide use of this agent to treat women with breast cancer where a common site of metastasis is the lung.

In certain embodiments of the invention, the above-described pharmaceutical compositions can comprise one or more of the inhibitors, and a second chemotherapeutic agent.

The term chemotherapeutic agent includes, without limitation, platinum-based agents, such as carboplatin and cisplatin; nitrogen mustard alkylating agents; nitrosourea alkylating agents, such as carmustine (BCNU) and other alkylating agents; antimetabolites, such as methotrexate; purine analog antimetabolites; pyrimidine analog antimetabolites, such as fluorouracil (5-FU) and gemcitabine; hormonal antineoplastics, such as goserelin, leuprolide, and tamoxifen; natural antineoplastics, such as taxanes (e.g., docetaxel and paclitaxel), aldesleukin, interleukin-2, etoposide (VP-16), interferon alfa, and tretinoin (ATRA); antibiotic natural antineoplastics, such as bleomycin, dactinomycin, daunorubicin, doxorubicin, and mitomycin; and vinca alkaloid natural antineoplastics, such as vinblastine and vincristine.

Further, the following additional drugs may also be used in combination with the antineoplastic agent, even if not considered antineoplastic agents themselves: dactinomycin;

daunorubicin HCl; docetaxel; doxorubicin HCl; epoetin alfa; etoposide (VP-16); ganciclovir sodium; gentamicin sulfate; interferon alfa; leuprolide acetate; meperidine HCl; methadone HCl; ranitidine HCl; vinblastin sulfate; and zidovudine (AZT). For example, fluorouracil has recently been formulated in conjunction with epinephrine and bovine collagen to form a particularly effective combination.

Still further, the following listing of amino acids, peptides, polypeptides, proteins, polysaccharides, and other large molecules may also be used: interleukins 1 through 18, including mutants and analogues; interferons or cytokines, such as interferons $\alpha$, $\beta$, and $\gamma$; hormones, such as luteinizing hormone releasing hormone (LHRH) and analogues and, gonadotropin releasing hormone (GnRH); growth factors, such as transforming growth factor-$\beta$ (TGF-$\beta$), fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), and insulin growth factor (IGF); tumor necrosis factor-$\alpha$ & $\beta$ (TNF-$\alpha$ & $\beta$); invasion inhibiting factor-2 (IIF-2); bone morphogenetic proteins 1-7 (BMP 1-7); somatostatin; Lhymosin-$\alpha$-1; $\gamma$-globulin; superoxide dismutase (SOD); complement factors; anti-angiogenesis factors; antigenic materials; and pro-drugs.

Preferred chemotherapeutic agents for use with the compositions and methods of treatment described herein include, but are not limited to altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interferon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine and vinorelbine tartrate.

All of the above drugs and additives may be added individually or in combination, as long as there is no negative interaction between or among the various drugs.

The anticancer(s) drug may be added to the saline solution before or after said cocktail buffer has been added to said saline solution. Alternatively, the anticancer drug may be added to said cocktail buffer before or after adding said ATP production inhibitor to said buffer.

In another preferred embodiment, the composition of the disclosure may comprise other biologically active substances, preferably a therapeutic drug or pro-drug, for example, other chemotherapeutic agents, scavenger compounds, antibiotics, anti-virals, anti-fungals, anti-inflammatories, vasoconstrictors and anticoagulants, antigens useful for cancer vaccine applications or corresponding pro-drugs.

Exemplary scavenger compounds include, but are not limited to thiol-containing compounds such as glutathione, thiourea, and cysteine; alcohols such as mannitol, substituted phenols; quinones, substituted phenols, aryl amines and nitro compounds.

Various forms of the chemotherapeutic agents and/or other biologically active agents may be used. These include, without limitation, such forms as uncharged molecules, molecular complexes, salts, ethers, esters, amides, and the like, which are biologically activated when implanted, injected or otherwise inserted into the tumor.

The methods of the present disclosure may be used to treat any cancerous tumor that is PET Positive and therefore is expected to have a high glycolytic rate. Highly glycolytic tumors may be located in almost any tissue including as examples brain, colon, urogenital, lung, renal, prostate, pancreas, liver, esophagus, stomach, hematopoietic, breast, thymus, testis, ovarian, skin, bone marrow or uterine tissue.

The pharmaceutical compositions of the present disclosure may be specially formulated for administration in solid or liquid form, including those adapted for the following: (1) oral administration, for example, drenches (aqueous or non-aqueous solutions or suspensions), pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a spray, cream or foam; (5) sublingually; (6) ocularly; (7) transdermally; or (8) nasally.

Of course, there will have to be the appropriate adjustments to the proposed solution or inhibitor when using the inhibitor for different parts of the body. For example, a topical application of the inhibitors might include a different cocktail composition consistent with the methodology contained herein.

In certain embodiments, the method comprises parenterally administering an effective amount of a subject pharmaceutical composition to a subject. In one embodiment, the method comprises intraarterial administration of a subject composition to a subject. In one embodiment, the method comprises intravenous (systemic) administration of a subject composition to a subject. In other embodiments, the method comprises administering an effective amount of a subject composition directly to the arterial blood supply of a cancerous tumor in a subject or directly to the tumor. In one embodiment, the method comprises administering an effective amount of a subject composition directly to the arterial blood supply of the cancerous tumor using a catheter. In embodiments where a catheter is used to administer a subject composition, the insertion of the catheter may be guided or observed by fluoroscopy or other method known in the art by which catheter insertion may be observed and/or guided. In another embodiment, the method comprises chemoembolization. For example a chemoembolization method may comprise blocking a vessel feeding the cancerous tumor with a composition comprised of a resin-like material mixed with an oil base (e.g., polyvinyl alcohol in Ethiodol) and one or more chemotherapeutic agents. In still other embodiments, the method comprises intraperitoneal or subcutaneous administration to a subject.

In certain embodiments, and as noted above, the methods of treating a cancerous tumor comprise administering one or more selective inhibitors of the disclosure in conjunction with a second agent to a subject. Such methods in certain embodiments comprise administering pharmaceutical compositions comprising one or more inhibitors in conjunction with other chemotherapeutic agents or scavenger compounds. Conjunctive therapy includes sequential, simultaneous and separate, or co-administration of the active compound in a way that the therapeutical effects of the first administered compound have not entirely disappeared when the subsequent treatment is administered. In one embodiment, the second agent can be a chemotherapeutic agent. In another embodiment, the second agent can be a scavenger compound. In certain embodiments, the second agent may be formulated into a separate pharmaceutical composition. In other embodiments, the pharmaceutical composition may comprise both an inhibitor and a second agent.

In other embodiments, the methods of treating a cancerous tumor comprise administering an effective amount of a subject composition directly to the blood vessels in the liver, head, neck, glands, or bones. For example, blood vessels such as the hepatic, femoral, cerebral, carotid, or vertebral arteries may be infused, injected, chemoembolized, or catheterized to administer the subject compositions to a cancerous tumor. In other embodiments, the methods comprise administering an effective amount of a subject composition directly to the blood vessels in a cancerous tumor in the head, neck, or bones. Such methods are well-known and used in the art. For example, Gobin, Y. P., et al. (2001) Radiology 218:724-732 (incorporated herein by reference) teaches a method for interarterial chemotherapy for brain tumors. Moser, et al. (2002) Head Neck 24:566-74 (incorporated herein by reference) reviews the use of intraarterial catheters for chemotherapeutic treatment in head and neck cancer. Wang, M. Q., et al. (2001) J. Vasc. Interv. Radiol. 12:731-7 (incorporated herein by reference) teaches a method of injecting the femoral arteries as well as a method of chemoembolization in order to treat osteosarcoma. Kato, T., et al. (1996) Cancer Chemother Pharmacol 37(4):289-96 (incorporated herein by reference) reviews the use of intraarterial infusion of microencapsulated anticancer drugs (chemoembolization) to treat cancerous tumors in the liver, kidney, intrapelvic organs, lung, head and neck, and bones. Hermann, K., et al. (2000) Radiology 215: 294-9; Kemeny, N. E., (1999) Baillieres Best Pract Res Clin Gastroenterol 13:593-610 (both incorporated herein by reference) describe exemplary methods of intraarterial and embolization methods for treatment of liver cancer.

In general, chemoembolization or direct intraarterial or intravenous injection therapy utilizing pharmaceutical compositions of the present disclosure can be typically performed in a similar manner, regardless of the site. Briefly, angiography (a road map of the blood vessels), or more specifically in certain embodiments, arteriography, of the area to be embolized may be first performed by injecting radiopaque contrast through a catheter inserted into an artery or vein (depending on the site to be embolized or injected) as an X-ray is taken. The catheter may be inserted either percutaneously or by surgery. The blood vessel may be then embolized by refluxing pharmaceutical compositions of the present disclosure through the catheter, until flow is observed to cease. Occlusion may be confirmed by repeating the angiogram. In embodiments where direct injection is used, the blood vessel is then infused with a pharmaceutical composition of the disclosure in the desired dose.

Embolization therapy generally results in the distribution of compositions containing inhibitors throughout the interstices of the tumor or vascular mass to be treated. The physical bulk of the embolic particles clogging the arterial lumen results in the occlusion of the blood supply. In addition to this effect, the presence of an anti-angiogenic factor(s) prevents the formation of new blood vessels to supply the tumor or vascular mass, enhancing the devitalizing effect of cutting off the blood supply. Direct intrarterial or intravenous generally results in distribution of compositions containing inhibitors throughout the interstices of the tumor or vascular mass to be treated as well. However, the blood supply is not generally expected to become occluded with this method.

Within one aspect of the present disclosure, primary and secondary tumors of the liver or other tissues may be treated utilizing embolization or direct intraarterial or intravenous injection therapy. Briefly, a catheter is inserted via the femoral or brachial artery and advanced into the hepatic artery by steering it through the arterial system under fluoroscopic guidance. The catheter is advanced into the hepatic arterial tree as far as necessary to allow complete blockage of the blood vessels supplying the tumor(s), while sparing as many of the arterial branches supplying normal structures as possible. Ideally this will be a segmental branch of the hepatic artery, but it could be that the entire hepatic artery distal to the origin of the gastroduodenal artery, or even multiple separate arteries, will need to be blocked depending on the extent of tumor and its individual blood supply. Once the desired catheter position is achieved, the artery is embolized by injecting compositions (as described above) through the arterial catheter until flow in the artery to be blocked ceases, preferably even after observation for 5 minutes. Occlusion of the artery may be confirmed by injecting radio-opaque contrast through the catheter and demonstrating by fluoroscopy or X-ray film that the vessel which previously filled with contrast no longer does so. In embodiments where direct injection is used, the artery is infused by injecting compositions (as described above) through the arterial catheter in a desired dose. The same procedure may be repeated with each feeding artery to be occluded.

For use in embolization therapy, compositions of the present disclosure can be preferably nontoxic, thrombogenic, easy to inject down vascular catheters, radio-opaque, rapid and permanent in effect, sterile, and readily available in different shapes or sizes at the time of the procedure. In addition, the compositions preferably result in the slow (ideally, over a period of several weeks to months) release of an inhibitor and/or a second agent. Particularly preferred compositions can have a predictable size of 15-200 microns after being injected into the vascular system. Preferably, they should not clump into larger particles either in solution or once injected. In addition, preferable compositions should not change shape or physical properties.

In most embodiments, the subject pharmaceutical compositions will incorporate the substance or substances to be delivered in an amount sufficient to deliver to a patient a therapeutically effective amount of an incorporated therapeutic agent or other material as part of a prophylactic or therapeutic treatment. The desired concentration of active compound in the particle will depend on absorption, inactivation, and excretion rates of the drug as well as the delivery rate of the compound. It is to be noted that dosage values may also vary with the severity of the condition to be alleviated. It is to be further understood that for any particular subject, specific dosage regimens can be adjusted over time according to the individual need and the professional judgment of the person administering or supervising the administration of the compositions. Typically, dosing will be determined using techniques known to one skilled in the art.

For the subject compositions, a range of dosage is contemplated by the present disclosure. The present disclosure contemplates embodiments that release at least those amounts over a three week period, at least twice those amounts over a six week period, etc. (i.e., other appropriate release frequencies).

Dosage may be based on the amount of the composition per kg body weight of the patient. For example, a range of amounts of compositions are contemplated, including about 0.001, 0.01, 0.1, 0.5, 1, 10, 15, 20, 25, 50 mg or more of such compositions per kg body weight of the patient. Other amounts will be known to those of skill in the art and readily determined.

In certain embodiments, the dosage of the subject compounds will generally be in the range of about 0.001 mg to about 10 mg per kg body weight, specifically in the range of about 0.1 mg to about 10 mg per kg, and more specifically in the range of about 0.1 mg to about 1 mg per kg. In one embodiment, the dosage can be in the range of about 0.3 mg to about 0.6 mg per kg. In another embodiment, the dosage can be in the range of about 0.4 mg to about 0.5 mg per kg.

Alternatively, the dosage of the subject disclosure may be determined by reference to the plasma concentrations of the composition. For example, the maximum plasma concentration (Cmax) and the area under the plasma concentration-time curve from time 0 to infinity (AUC (0-4)) may be used. Dosages for the present disclosure include those that produce the above values for Cmax and AUC (0-4) and other dosages resulting in larger or smaller values for those parameters.

Actual dosage levels of the active ingredients in the pharmaceutical compositions of this disclosure may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present disclosure employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In general, a suitable daily dose of a compound of the disclosure will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The precise time of administration and amount of any particular compound that will yield the most effective treatment in a given patient will depend upon the activity, pharmacokinetics, and bioavailability of a particular compound, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during a 24-hour period. Treatment, including supplement, amounts, times of administration and formulation, may be optimized according to the results of such monitoring. The patient may be periodically reevaluated to determine the extent of improvement by measuring the same parameters, the first such reevaluation typically occurring at the end of four weeks from the onset of therapy, and subsequent reevaluations occurring every four to eight weeks during therapy and then every three months thereafter. Therapy may continue for several months or even years, with a minimum of one month being a typical length of therapy for humans. Adjustments to the amount(s) of agent administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The combined use of several compounds of the present disclosure, or alternatively other chemotherapeutic agents, may reduce the required dosage for any individual component because the onset and duration of effect of the different components may be complimentary. In such combined therapy, the different active agents may be delivered together or separately, and simultaneously or at different times within the day.

Toxicity and therapeutic efficacy of subject compounds may be determined by standard pharmaceutical procedures in cell cultures or experimental animals, e.g., for determining the $LD_{50}$ (dose killing 50%) and the $ED_{50}$ (effective medium dose). Compositions that exhibit large therapeutic indices are preferred. Although compounds that exhibit toxic side effects may be used, care should be taken to design a delivery system that targets the compounds to the desired site in order to reduce side effects.

The data obtained from the cell culture assays and animal studies may be used in formulating a range of dosage for use in humans. The dosage of any supplement, or alternatively of any components therein, lies preferably within a range of circulating concentrations that include the $ED_{50}$ with little or no toxicity. The dosage may vary within this range depending upon the dosage form employed and the route of administration utilized. For agents of the present disclosure, the therapeutically effective dose may be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information may be used to more accurately determine useful doses in humans. Levels in plasma may be measured, for example, by high performance liquid chromatography.

The cocktail for the inhibitors can be prepared just prior to use, or it can be part of a kit. The liquid cocktail or buffer can be sold in "dry form" along with the filter and the inhibitor, or a liquid sterile version of the buffer can be sold, with or without an inhibitor already added. Dilution would take place at the time of use.

If more than one inhibitor that requires the buffer is to be used, the additional inhibitor(s) can be added to the cocktail at the same time as the first inhibitor is added. If any additional cancer fighting drugs are to be used, those drugs may be added to the diluted mixture, just prior to use.

While this disclosure has been described with reference to specific embodiments, it will be recognized by those skilled in the art that variations are possible without departing from the spirit and scope of the disclosure, and that it is intended to cover all changes and modifications of the disclosure disclosed herein for the purposes of illustration which do not constitute departure from the spirit and scope of the disclosure.

What is claimed is:

1. A method for the treatment of cancer, said method comprising the steps of:
   a) preparing a cocktail buffer having at least one sugar and a buffer;
   b) adding at least one inhibitor to said cocktail buffer having the following formula

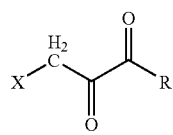

wherein X is selected from the group consisting of: a halide, sulfonate, a carboxylate, an alkoxide, and amine oxide; and R is selected from the group consisting of: OR', N(R")$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C 12 aryl or C(O)R''', R" represents H, C1-C 6 alkyl, or C6-C12 aryl, and R''' represents H, C1-C20 alkyl or C6-C12 aryl; forming an inhibitor cocktail buffer;
   c) diluting said inhibitor cocktail buffer by adding said buffer to a saline solution; and
   d) administering said diluted inhibitor-cocktail buffer to a patient;
   wherein said cancer is a cancerous tumor that is positron emission tomography (PET) positive.

2. The method according to claim 1, wherein said buffer is a non-potassium containing buffer.

3. The method according to claim 2, wherein said non-potassium containing buffer is comprised of a sodium phosphate buffer.

4. The method according to claim 1, wherein said at least one sugar is two sugars.

5. The method according to claim 1, wherein said at least one sugar is three sugars.

6. The method according to claim 5, wherein at least one of the sugars is a five carbon sugar.

7. The method according to claim 6, wherein at least two of the sugars are a five carbon sugar.

8. The method according to claim 7, wherein said five carbon sugars are independently selected from the group consisting of mannitol, erytritol, isomalt, lactitol, maltitol, xyolitol, dulcitol, ribitol, inositol, sorbitol, and combinations thereof.

9. The method according to claim 5, wherein at least one of said sugars is glycerol.

10. The method according to claim 5, wherein each of said sugars may be added in a volume up to a maximum solubility of said sugar.

11. The method according to claim 5, wherein said sugars are glycerol, inositol, and sorbitol.

12. The method according to claim 11, wherein said cocktail buffer comprises said glycerol in a range from about 0.1% to about 3%, said inositol in a range from about 1% to about 5%, and said sorbitol in a range from about 30% to about 50%.

13. The method according to claim 1, wherein R of formula (I) is OH and X of formula (I) is selected from the group consisting of: a halide, a sulfonate, a carboxylate, an alkoxide, and an amine oxide.

14. The method according to claim 13, wherein X is a halide selected from the group consisting of: fluoride, bromide, chloride, and iodide.

15. The method according to claim 14, wherein the inhibitor is a 3-halopyruvate selected from the group consisting of: 3-fluoropyruvate, 3-chloropyruvate, 3-bromopyruvate, 3-iodopyruvate, and combinations thereof.

16. The method according to claim 13, wherein X is a sulfonate selected from the group consisting of: triflate, mesylate and tosylate.

17. The method according to claim 12, wherein X is an amine oxide.

18. The method according to claim 17, wherein the amine oxide is dimethylamine oxide.

19. The method according to claim 1, further comprising the step of adding an anticancer drug to said saline solution before said inhibitor cocktail buffer has been added to said saline solution.

20. The method according to claim 1, further comprising the step of adding an anticancer drug to said saline solution after said inhibitor cocktail buffer has been added to said saline solution.

21. The method according to claim 1, further comprising the step of adding an anticancer drug to said cocktail buffer prior to adding said inhibitor to said buffer.

22. The method according to claim 1, further comprising the step of adding an anticancer drug to said inhibitor cocktail buffer after said inhibitor has been added to said buffer.

23. The method according to claim 1, further comprising the step of adding an additional anticancer agent to said cocktail buffer, said additional anticancer agent being selected from the group consisting of: platinum-based agents, nitrogen mustard alkylating agents, nitrosourea alkylating agents, antimetabolites, pyrimidine antimetabolites, hormonal antineoplastics, natural antineoplastics, antibiotic natural antineoplastics, vinca alkaloid natural antineoplastics, dactinomycin, daunorubicin HCl, docetaxel, doxorubicin HCl, epoetin alfa, etoposide (VP-16), ganciclovir sodium, gentamicin sulfate, interferon alfa, leuprolide acetate, meperidine HCl, methadone HCl, ranitidine,HCl, vinblastin sulfate, zidovudine, interleukins 1 through 18, mutants of interleukins 1 through 18, interferons, cytokines, hormones, growth factors, fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF),insulin growth factor (IGF), tumor necrosis factor-α & β (TNF-α & β), invasion inhibiting factor-2 (IIF-2), bone morphogenetic proteins 1-7 (BMP 1-7), somatostatin, Lhymosin-α-1,γ-globulin, superoxide dismutase (SOD), complement factors, anti-angiogenesis factors, antigenic materials, pro-drugs, altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin--dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interferon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine, vinorelbine tartrate, and combinations thereof.

24. The method according to claim 1, further comprising the step of adding an additional anticancer agent to said saline solution, said additional anticancer agent being selected from the group consisting of: platinum-based agents, nitrogen mustard alkylating agents, nitrosourea alkylating agents, antimetabolites, pyrimidine antimetabolites, hormonal antineoplastics, natural antineoplastics, antibiotic natural antineoplastics, vinca alkaloid natural antineoplastics, dactinomycin, daunorubicin HCl, docetaxel, doxorubicin HCl, epoetin alfa, etoposide (VP-16), ganciclovir sodium, gentamicin sulfate, interferon alfa, leuprolide acetate, meperidine HCl, methadone HCl, ranitidine HCl, vinblastin sulfate, zidovudine, interleukins 1 through 18, mutants of interleukins 1 through 18, interferons, cytokines, hormones, growth factors, fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), tumor necrosis factor-α & β (TNF-α & β), invasion inhibiting factor-2 (IIF-2), bone morphogenetic proteins 1-7 (BMP 1-7), somatostatin, Lhymosin-α-1,γ-globulin, superoxide dismutase (SOD), complement factors, anti-angiogenesis factors, antigenic materials, pro-drugs, altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin--dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interferon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine, vinorelbine tartrate, and combinations thereof.

25. The method according to claim 1, wherein the inhibitor cocktail buffer retains at least 50% of the inhibitor in active form after 2 hours.

26. The method according to claim 1, wherein the inhibitor cocktail buffer retains at least 95% of the inhibitor in active form after 2 hours.

27. A composition for the treatment of cancer, wherein said composition is an inhibitor cocktail buffer formed by a method comprising the steps of:
a) preparing a cocktail buffer having at least one sugar and a buffer; and
b) adding at least one inhibitor to said cocktail buffer having the following formula

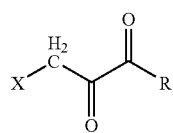

(I)

wherein X is selected from the group consisting of: a halide, sulfonate, a carboxylate, an alkoxide, and amine oxide; and R is selected from the group consisting of: OR', N(R'')$_2$, C(O)R''', C1-C6 alkyl, C6-C12 aryl, C1-C6 heteroalkyl, a C6-C12 heteroaryl, H, and an alkali metal; where R' represents H, alkali metal, C1-C6 alkyl, C6-C12 aryl or C(O)R''', R'' represents H, C1-C6 alkyl, or C6-C12 aryl, and R''' represents H, C1-C20 alkyl or C6-C12 aryl; forming said inhibitor cocktail buffer; and
wherein said cancer is a cancerous tumor that is positron emission tomography (PET) positive.

28. The composition according to claim 27, wherein said buffer is a non-potassium containing buffer.

29. The composition according to claim 28, wherein said non-potassium containing buffer is comprised of a sodium phosphate buffer.

30. The composition according to claim 27, wherein said at least one sugar is two sugars.

31. The composition according to claim 27, wherein said at least one sugar is three sugars.

32. The composition according to claim 31, wherein at least one of the sugars is a five carbon sugar.

33. The composition according to claim 32, wherein at least two of the sugars are a five carbon sugar.

34. The composition according to claim 33, wherein said five carbon sugars are independently selected from the group consisting of mannitol, erytritol, isomalt, lactitol, maltitol, xyolitol, dulcitol, ribitol, inositol, sorbitol, and combinations thereof.

35. The composition according to claim 31, wherein each of said sugars may be added in a volume up to a maximum solubility of said sugar.

36. The composition according to claim 31, wherein at least one of said sugars is glycerol.

37. The composition according to claim 31, wherein said sugars are glycerol, inositol, and sorbitol.

38. The composition according to claim 37, wherein said cocktail buffer comprises said glycerol in a range from about 0.1% to about 3%, said inositol in a range from about 1% to about 5%, and said sorbitol in a range from about 30% to about 50%.

39. The composition according to claim 27, wherein R of formula (I) is OH and X of formula (I) is selected from the group consisting of: a halide, a sulfonate, a carboxylate, an alkoxide, and an amine oxide.

40. The composition according to claim 39, wherein X is a halide selected from the group consisting of: fluoride, bromide, chloride, and iodide.

41. The composition according to claim 40, wherein the inhibitor is a 3-halopyruvate selected from the group consisting of: 3-fluoropyruvate, 3-chloropyruvate, 3-bromopyruvate, 3-iodopyruvate, and combinations thereof.

42. The composition according to claim 39, wherein X is a sulfonate selected from the group consisting of: triflate, mesylate and tosylate.

43. The composition according to claim 39, wherein X is an amine oxide.

44. The composition according to claim 43, wherein the amine oxide is dimethylamine oxide.

45. The composition according to claim 27, further comprising the step of adding an anticancer drug to said saline solution before said inhibitor cocktail buffer has been added to said saline solution.

46. The composition according to claim 27, further comprising the step of adding an anticancer drug to said saline solution after said inhibitor cocktail buffer has been added to said saline solution.

47. The composition according to claim 27, further comprising the step of adding an anticancer drug to said cocktail buffer prior to adding said inhibitor to said buffer.

48. The composition according to claim 27, further comprising the step of adding an anticancer drug to said inhibitor cocktail buffer after said inhibitor has been added to said buffer.

49. The composition according to claim 27, further comprising the step of adding an additional anticancer agent to said cocktail buffer, said additional anticancer agent being selected from the group consisting of: platinum-based agents, nitrogen mustard alkylating agents, nitrosourea alkylating agents, antimetabolites, pyrimidine antimetabolites, hormonal antineoplastics, natural antineoplastics, antibiotic natural antineoplastics, vinca alkaloid natural antineoplastics, dactinomycin, daunorubicin HCl, docetaxel, doxorubicin HCl, epoetin alfa, etoposide (VP-16), ganciclovir sodium, gentamicin sulfate, interferon alfa, leuprolide acetate, meperidine HCl, methadone HCl, ranitidine HCl, vinblastin sulfate, zidovudine, interleukins 1 through 18, mutants of interleukins 1 through 18, interferons, cytokines, hormones, growth factors, fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF),insulin growth factor (IGF), tumor necrosis factor-$\alpha$ & $\beta$ (TNF-$\alpha$ & $\beta$), invasion inhibiting factor-2 (IIF-2), bone morphogenetic proteins 1-7 (BMP 1-7), somatostatin, Lhymosin-$\alpha$-1,$\gamma$-globulin, superoxide dismutase (SOD), complement factors, anti-angiogenesis factors, antigenic materials, pro-drugs, altretamine, asparaginase, BCG, bleomycin sulfate, busul fan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interferon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine, vinorelbine tartrate, and combinations thereof.

50. The composition according to claim 27, further comprising the step of adding an additional anticancer agent to said saline solution, said additional anticancer agent being selected from the group consisting of: platinum-based agents, nitrogen mustard alkylating agents, nitrosourea alkylating agents, antimetabolites, pyrimidine antimetabolites, hormonal antineoplastics, natural antineoplastics, antibiotic natural antineoplastics, vinca alkaloid natural antineoplastics, dactinomycin, daunorubicin HCl, docetaxel, doxorubicin HCl, epoetin alfa, etoposide (VP-16), ganciclovir sodium, gentamicin sulfate, interferon alfa, leuprolide acetate, meperidine HCl, methadone HCl, ranitidine HCl, vinblastin sulfate, zidovudine, interleukins 1 through 18, mutants of interleukins 1through 18, interferons, cytokines, hormones, growth factors, fibroblast growth factor (FGF), nerve growth factor (NGF), growth hormone releasing factor (GHRF), epidermal growth factor (EGF), fibroblast growth factor homologous factor (FGFHF), hepatocyte growth factor (HGF),insulin growth factor (IGF), tumor necrosis factor-$\alpha$ & $\beta$ (TNF-$\alpha$ & $\beta$), invasion inhibiting factor-2 (IIF-2), bone morphogenetic proteins 1-7 (BMP 1-7), somatostatin, Lhymosin-$\alpha$-1,$\gamma$-globulin, superoxide dismutase (SOD), complement factors, anti-angiogenesis factors, antigenic materials, pro-drugs, altretamine, asparaginase, BCG, bleomycin sulfate, busulfan, carboplatin, carmusine, chlorambucil, cisplatin, claladribine, 2-chlorodeoxyadenosine, cyclophosphamide, cytarabine, dacarbazine imidazole carboxamide, dactinomycin, daunorubicin-dunomycin, dexamethosone, doxurubicin, etoposide, floxuridine, fluorouracil, fluoxymesterone, flutamide, fludarabine, goserelin, hydroxyurea, idarubicin HCL, ifosfamide, interferon alfa, interferon alfa 2a, interferon alfa 2b, interferon alfa n3, irinotecan, leucovorin calcium, leuprolide, levamisole, lomustine, megestrol, melphalan, L-sarcosylin, melphalan hydrochloride, MESNA, mechlorethamine, methotrexate, mitomycin, mitoxantrone, mercaptopurine, paclitaxel, plicamycin, prednisone, procarbazine, streptozocin, tamoxifen, 6-thioguanine, thiotepa, vinblastine, vincristine, vinorelbine tartrate, and combinations thereof.

51. The composition according to claim 27, wherein the inhibitor cocktail buffer retains at least 50% of the inhibitor in active form after 2 hours.

52. The composition according to claim 27, wherein the inhibitor cocktail buffer retains at least 95% of the inhibitor in active form after 2 hours.

53. The method according to claim 1, wherein the cancerous tumor is in a tissue selected from the group consisting of brain, colon, urogenital, lung, renal, prostate, pancreas, liver, esophagus, stomach, hematopoietic, breast, thymus, testis, ovarian, skin, bone marrow, and uterine.

54. The composition according to claim 27, wherein the cancerous tumor is in a tissue selected from the group consisting of brain, colon, urogenital, lung, renal, prostate, pancreas, liver, esophagus, stomach, hematopoietic, breast, thymus, testis, ovarian, skin, bone marrow, and uterine.

* * * * *